(12) United States Patent
Ramabadran (10) Patent No.: US 9,032,699 B2
(45) Date of Patent: May 19, 2015

(54) PATHOGEN REDUCTION SYSTEM FOR THE PREPARATION OF FOOD PRODUCTS

(75) Inventor: Arun Ramabadran, Oswego, IL (US)

(73) Assignee: Spraying Systems Co., Wheaton, IL (US)

( * ) Notice: Subject to any disclaimer, the term of this patent is extended or adjusted under 35 U.S.C. 154(b) by 648 days.

(21) Appl. No.: 13/101,599

(22) Filed: May 5, 2011

(65) Prior Publication Data

US 2011/0265431 A1 Nov. 3, 2011

Related U.S. Application Data

(63) Continuation-in-part of application No. PCT/US2009/042291, filed on Apr. 30, 2009.

(60) Provisional application No. 61/111,566, filed on Nov. 5, 2008.

(51) Int. Cl.
| | | |
|---|---|---|
| *A23B 4/18* | (2006.01) | |
| *A23B 4/30* | (2006.01) | |
| *A23L 3/3418* | (2006.01) | |

(Continued)

(52) U.S. Cl.
CPC ... *A23B 4/18* (2013.01); *A23B 4/30* (2013.01); *A23L 3/3418* (2013.01); *A23L 3/3454* (2013.01); *A23L 3/3589* (2013.01); *A61L 2/22* (2013.01); *A61L 2202/14* (2013.01); *B26D 1/00* (2013.01); *B26D 7/0608* (2013.01); *B26D 7/0683* (2013.01); *B26D 7/34* (2013.01); *B26D 2007/0025* (2013.01); *B26D 2210/02* (2013.01); *B65B 25/065* (2013.01); *B65B 55/10* (2013.01); *B65B 55/18* (2013.01)

(58) Field of Classification Search
USPC ......... 53/111 R, 513, 514, 517, 111 RC, 428, 53/431
IPC ....................... A23B 4/18; A23L 3/3589; B65B 25/065, 55/18, 55/10
See application file for complete search history.

(56) References Cited

U.S. PATENT DOCUMENTS

| | | |
|---|---|---|
| 3,927,588 A | 12/1975 | Laderach |
| 4,560,567 A * | 12/1985 | Rausing ........................ 426/399 |

(Continued)

FOREIGN PATENT DOCUMENTS

WO    WO 2010/053595 A1    5/2010

OTHER PUBLICATIONS

International Search Report dated Jun. 30, 2009 of International Application No. PCT/US2009/42291, filed Apr. 30, 2009.

(Continued)

*Primary Examiner* — Christopher Harmon
(74) *Attorney, Agent, or Firm* — Leydig, Voit & Mayer, Ltd.

(57) ABSTRACT

A system for preparing food product minimizes bacterial contamination and outgrowth within the packaged food product, includes a powered slicer to sequentially separate slices of food product to create a stack of food product slices. The system also includes a first spray nozzle for depositing a first predetermined amount of the antimicrobial preparation onto the first face of the log or other food product piece each time a slice is removed as well as a a second spray nozzle for depositing a second predetermined amount of the antimicrobial preparation into a vacuum pouch prior to reception of a stack within the pouch. In an embodiment, the spray system is implemented with respect to a mixer/blender to pretreat a mix prior to further processing.

20 Claims, 9 Drawing Sheets

(51) Int. Cl.
*A23L 3/3454* (2006.01)
*A23L 3/3589* (2006.01)
B26D 1/00 (2006.01)
B26D 7/34 (2006.01)
*A61L 2/22* (2006.01)
*B26D 7/06* (2006.01)
*B26D 7/00* (2006.01)
*B65B 25/06* (2006.01)
*B65B 55/10* (2006.01)
*B65B 55/18* (2006.01)

(56) References Cited

U.S. PATENT DOCUMENTS

| | | | | |
|---|---|---|---|---|
| 4,712,458 | A * | 12/1987 | Mally | 83/86 |
| 5,802,959 | A | 9/1998 | Benson et al. | |
| 6,279,302 | B1 * | 8/2001 | Kuchler | 53/517 |
| 6,645,429 | B1 | 11/2003 | Raniwala | |
| 6,964,787 | B2 | 11/2005 | Swart et al. | |
| 7,247,330 | B2 * | 7/2007 | Kuethe et al. | 426/325 |
| 7,976,885 | B2 * | 7/2011 | Pulsfus et al. | 426/316 |
| 2004/0018284 | A1 * | 1/2004 | Kuethe et al. | 426/326 |
| 2004/0101604 | A1 * | 5/2004 | Granly Koch et al. | 426/335 |
| 2006/0216384 | A1 * | 9/2006 | Gore | 426/518 |
| 2006/0219069 | A1 * | 10/2006 | Skaar et al. | 83/13 |
| 2006/0225547 | A1 | 10/2006 | Stanojevic et al. | |
| 2007/0020366 | A1 * | 1/2007 | Luchansky et al. | 426/335 |
| 2010/0247722 | A1 * | 9/2010 | Luchansky et al. | 426/281 |

OTHER PUBLICATIONS

European Patent Office, Supplementary European Search Report in European Patent Application No. 09825145.7 (Mar. 27, 2012).

United States Patent and Trademark Office, International Search Report in the International Patent Application No. PCT/US2012/036313 (Oct. 4, 2012).

United States Patent and Trademark Office, International Preliminary Report on Patentability in the International Patent Application No. PCT/US2012/036313 (Nov. 14, 2013).

* cited by examiner

PATHOGEN REDUCTION SYSTEM FOR THE PREPARATION OF FOOD PRODUCTS

CROSS-REFERENCE TO RELATED APPLICATIONS

This patent application claims the benefit of PCT US/09/42291, filed Apr. 30, 2009, which claims the benefit of U.S. Provisional Patent Application No. 61/111,566, filed Nov. 5, 2008, both of which are herein incorporated by reference in their entirety for all that they teach without exclusion of any portion thereof.

BACKGROUND OF THE INVENTION

When sliced meat products are stored, e.g., during transportation, on the store shelf prior to sale, or in the consumer's home, bacteria present in the product tend to multiply over time, eventually causing an unsafe condition for the consumer. In particular, certain bacterial and other pathogenic contaminations can be injurious or even deadly to humans. For example, various strains of *E. coli.* and *Listeria* bacteria have been known, when food-borne, to cause outbreaks of especially serious illnesses, especially in very young and very old consumers.

The predominant technique for controlling bacterial contamination in modern meat processing plants has been to disinfect the equipment that comes into contact with the food product, while maintaining high sanitation standards for production personnel, so as to minimize the transfer of bacteria. However, this technique does not necessarily eliminate bacteria already present on the food product, and does not treat contamination that may occur between equipment cleaning cycles.

OBJECTS AND SUMMARY OF THE INVENTION

It is an object of the present invention to provide a food processing system and apparatus including a spraying apparatus with multiple spray heads throughout the system for controlling pathogenic contamination, eliminating a potential source of biological hazard for consumers.

Another object is to provide a food product processing system and apparatus as characterized above which can be operated on a substantially uninterrupted basis, without the need to frequently shut down the system for equipment cleaning.

A further object is to provide a processing system and apparatus of the foregoing type in which unintended disruption or malfunction of the spray components can be detected and an alarm provided to the operator of the system.

Other objects and advantages of the invention will become apparent upon reading the following detailed description and upon reference to the drawings, of which:

DETAILED DESCRIPTION OF THE INVENTION

Bacterial contamination within a meat processing plant is a constant problem that must be addressed for the safety of the consumer. It is impossible to eliminate all bacteria in any processing plant, but it is possible to minimize contamination and control the growth of bacteria that remain. The extent of bacterial contamination in any given setting is typically referred to as "bacterial load." While the danger posed by a specific bacterial load is largely dependent on the type of bacteria in question, it is generally desirable to minimize bacterial load in a food processing plant or facility.

In today's food processing plants, many steps are taken in an attempt to minimize bacterial load in the finished food product. For example stringent standards for worker hygiene are enforced, and production equipment and areas are frequently cleaned and sterilized. Nonetheless, it is still all too common to have bacteria transferred to the product during processing prior to packaging. One particular piece of equipment in which bacterial load is difficult to control is within a deli meat slicer. Such devices have many surfaces and niches within which bacteria may be harbored. Such areas include grippers, inlet conveyors, product transfer conveyors, blades, and outlet conveyors. Moreover, the surface area of exposed meat provides another host for bacterial outgrowth in this application.

Figure 1:
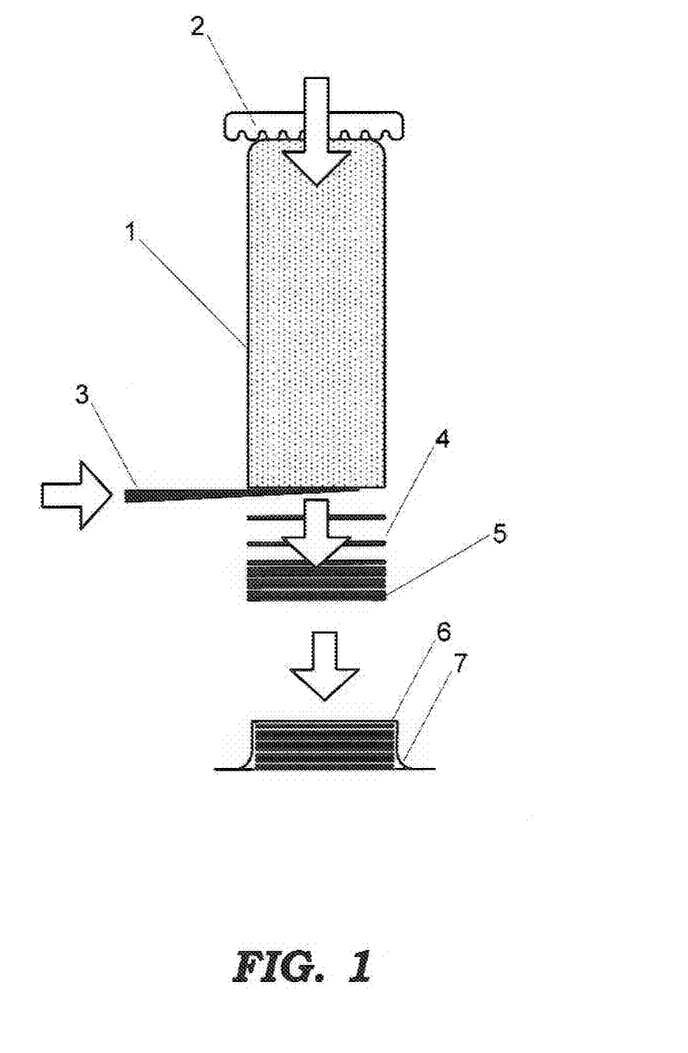
FIG. 1 is a schematic overview diagram of a generic meat slicing process within which the present invention may be implemented.

Referring more specifically to the figures, FIG. 1 shows a schematic overview diagram of a generic meat slicing process within which the present invention may be implemented. In general, a log 1 of food material such as meat, cheese, etc., is placed within the device in contact with a support 2. The log 1 typically rests on a table, conveyor, or platform, not shown. The function of the support 2 is to advance the log 1 into a slicer blade 3, shown schematically. The slicer blade 3 may be an oscillating straight blade, a rotating curved blade, or any other suitable blade, depending upon the cutting requirements imposed by the log 1 material and the speed of processing, as well as other factors potentially.

As the log 1 is advanced by the support 2 into the slicer blade 3, slices 4 of the log 1 are removed and accumulated, e.g., in a stack 5. When the stack 5 reaches a certain size or quantity, the finished stack 6 is moved away from the log 1 and is packaged within a package 7. The packaging may take any one of various known forms, but one often-used packaging type is the vacuum pack. This type of packaging generally employs a flexible envelope 7, alone or in conjunction with a backing piece. The finished stack 6 is inserted in the envelope 7, after which the envelope 7 is evacuated to a suitable vacuum level and sealed. The envelope 7 may also be backfilled with an inert gas if desired after evacuation.

Figure 2:
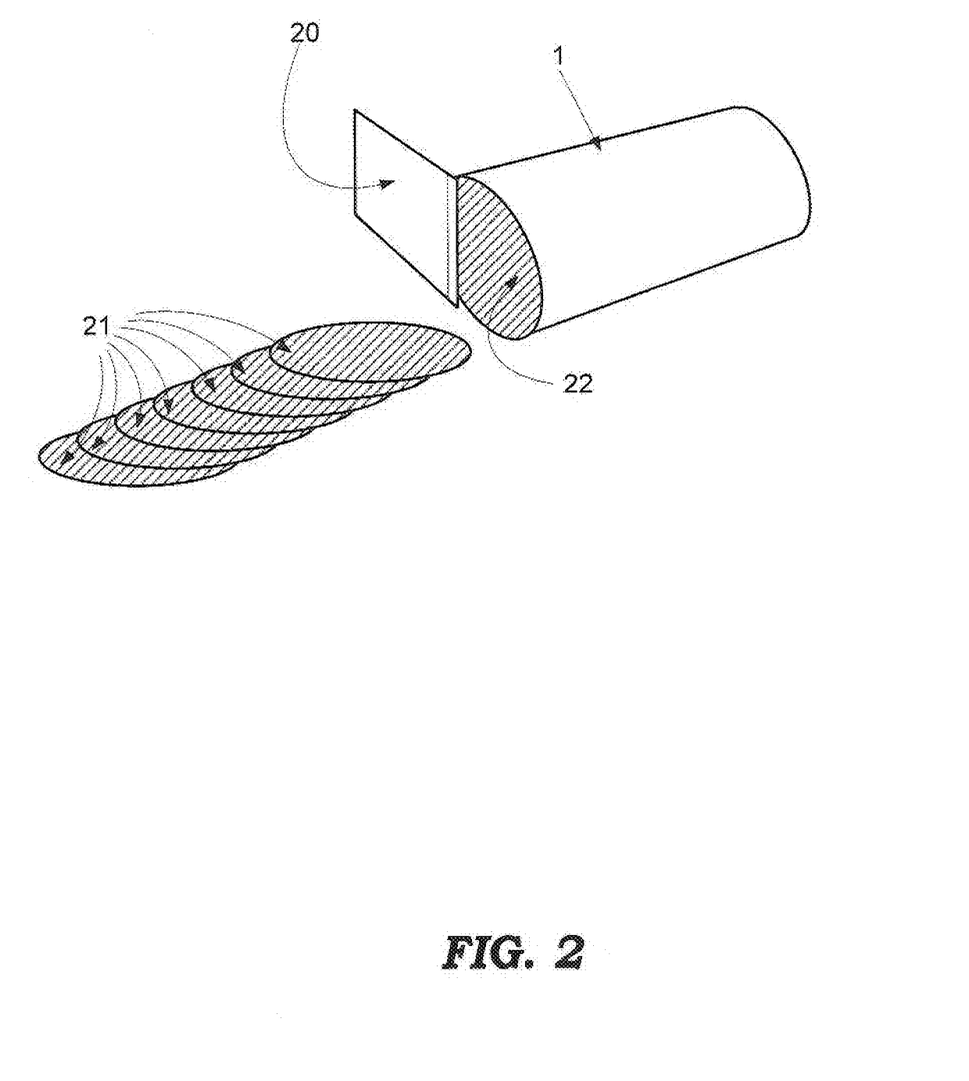
FIG. 2 is a perspective view of a generic cutting operation, showing the surfaces exposed during the operation.

Having reviewed the basic slicing and packaging operation as it exists, the potential sources of contamination will be discussed with reference to FIG. 2. As can be seen, FIG. 2 illustrates a perspective view of a generic cutting operation, showing the surfaces exposed during the operation. As the slicer blade 3 removes each slice 4 from the log 1, a number of surfaces are exposed for contamination or cross-contamination. In particular, each slice 4 presents a front surface 21, and a back surface (not shown). In addition, the exposed face 22 of the log 1 can receive bacteria from the blade 20, or can pass bacteria to the blade 20 to be deposited onto a subsequent slice. Thus, whereas the uncut log 1 exposes only a single outer surface, the sliced log 1 and slicer parts significantly multiply the number of surfaces on which contamination must be controlled.

In an embodiment of the invention, an antimicrobial fluid is applied, in a specifically controlled sequence, onto the various exposed faces of the processed food product during processing. From the teachings herein, it will be appreciated that it is desirable to apply a certain amount of the antimicrobial fluid, and to avoid applying substantially more or substantially less than that predetermined amount. In particular, the use of too little antimicrobial fluid raises the risk that the bacterial load may not be appropriately controlled, whereas the use of too much antimicrobial fluid increases the cost of the processing operation and unnecessarily exposes the consumer to an excess of chemicals.

The inventor has discovered that spraying the antimicrobial preparation onto the face of each slice as it is created with approximately 80% coverage of the surface area is effective to yield full coverage when the slice is stacked and further processed as discussed herein. As each sprayed slice falls onto the previous slice, the back end of that slice is coated with the antimicrobial preparation as well, via contact with the next slice to fall on the stack. In an embodiment of the invention, each shot is dispensed only when the slicer is cutting meat and is applied to the face of the meat in between each revolution or oscillation of the slicing blade. In a further embodiment of the invention, the system accommodates blade speeds from 0-1500 RPM, i.e., up to 1500 slices per minute.

Once each slice in a stack of food product, e.g., deli meat, (typically 6-12 slices) has been sprayed, the same system will also dispense another small shot of antimicrobial preparation into a vacuum pouch, e.g., created by a rollstock machine. The rollstock packaging machine or other system for providing the vacuum packaging is located at the outlet end of the slicing system in an embodiment of the invention. The additional amount of antimicrobial preparation acts to treat the bottom, top, and sides of the packaged stack. Although the antimicrobial preparation is added to the package before insertion of the stack, as a vacuum is drawn to seal the package, the antimicrobial is dispersed across the surface area of the stack.

Figure 3:
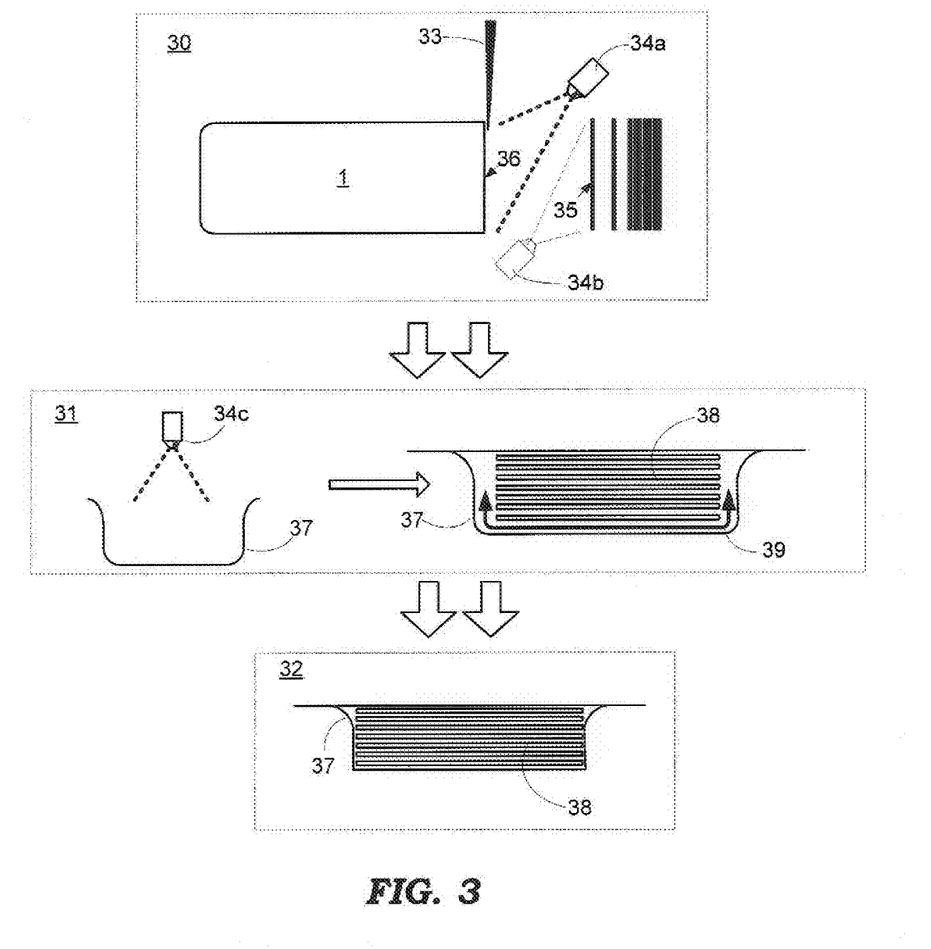
FIG. 3 is a schematic diagram of a meat slicing system according to an embodiment of the present invention.

In keeping with the preceding discussion, FIG. 3 shows a schematic diagram of a meat slicing system according to an embodiment of the present invention. The system is divided into a slicing stage 30, a packaging phase 31, and a finishing stage 32. Although these stages 30, 31, 32 may operate continuously and simultaneously, they can be considered to operate sequentially with respect to a given slice stack. Moreover, it will be appreciated that although only one processing chain is shown, it is contemplated in an embodiment of the invention that multiple processing chains like that shown in FIG. 3 will be run simultaneously.

At the slicing stage 31, a slicer blade 33 produces sequential slices of a food product from a log 1 as discussed above. However, in addition, a first spray nozzle 34a located adjacent the log 1 (but out of the path of travel for the slices) sprays a shot of antimicrobial preparation on the exposed face 36 of the log 1. This face 36 will become the rear side of the next slice to be removed from the log 1. In an optional embodiment of the invention, as each slice is removed, a second optional spray nozzle 34b may apply a second shot of antimicrobial preparation to the reverse side 35 of the slice.

In an embodiment of the invention, the first and second spray nozzles 34a, 34b are triggered intermittently by an optical or other sensor or output (not shown) that provides a signal indicating the position of the blade 33. In another embodiment, an encoder signal from the slicer is used to establish position of the blade, and thus is used to set the window and timing of the shot. Thus, for example, when the blade 33 is in a first position A so as to expose the face 36 of the log 1, the first spray nozzle 34a is activated for a predetermined burst period. As each slice falls away from the log 1 (e.g., when the blade 33 is in a second position B obscuring the face 36 of the log 1, the second spray nozzle 34b is activated for a second predetermined burst period. When the second burst is applied, the removed slice may be either on the stack in progress or in transit to the stack. Except for the first and last slices in the stack, when each slice contacts the stack in progress, the antimicrobial preparation on the surfaces 36, 35 of the slice is spread by contact with the preceding and following slices respectively.

As each stack is completed, it is moved to a packaging area (which may be adjacent the slicing area) where a packaging operation 31 is executed. As part of the packaging operation 31, a third spray nozzle 34c provides a shot of antimicrobial preparation into a vacuum rollstock pouch 37. The timing of this shot from the third spray nozzle 34c is not dependent upon the timing of the blade 33 or the other spray nozzles 34a, 34b. Rather, it is just necessary to execute the shot from the third spray nozzle 34c sometime prior to packaging the stack. The signal for triggering this third shot may be derived from the rollstock machine itself rather than a push button or external sensor in an embodiment of the invention.

Once the stack 38 is in the packaging area and the shot from the third spray nozzle 34c has been executed, the stack 38 is inserted into the vacuum pouch 37 as shown in stage 31. Subsequently, a vacuum is applied to the interior of the pouch 37. The applied vacuum causes the antimicrobial preparation 39 deposited by the shot from the third spray nozzle 34c to be drawn across the surface of the stack 37, coating any external surfaces that may not have been reached by the shots from the first spray nozzle 34a and the optional second spray nozzle 34b. Once the appropriate vacuum has been drawn, the vacuum pouch 37 is sealed at the sealing stage 32.

Having discussed the overall structure and operation of the system, the control and communication architecture of the system will be discussed in greater detail with reference to FIG. 4. As will be appreciated, FIG. 4 is a system schematic corresponding to a system within an embodiment of the present invention, including elements for user input and output, spray control, packaging control, and alarm control.

Figure 4:
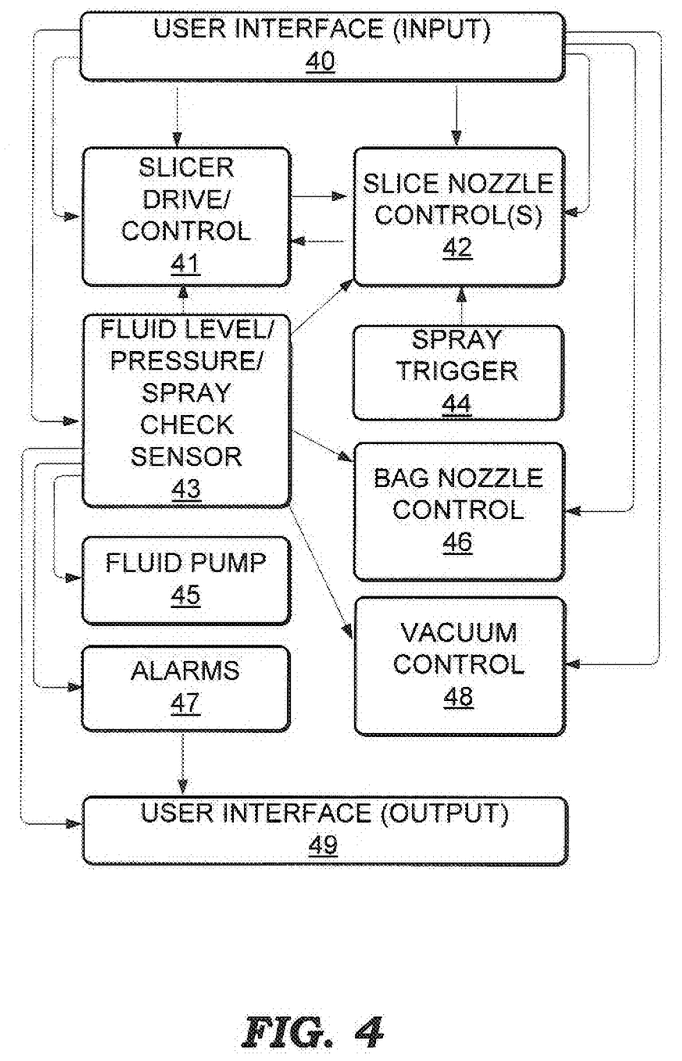
FIG. 4 is a system schematic corresponding to a system within an embodiment of the present invention, including elements for user input and output, spray control, packaging control, and alarm control.

The system illustrated in FIG. 4 includes an input user interface 40 for receiving input from a system operator, e.g., to start and stop processes, to set alarm levels and spray shot durations, etc. An output user interface 49 is included in the system to provide information to the user, e.g., feedback as values are entered in the input interface 40, alarms during operations, and other signaling and informational output.

In order to execute the user-programmed operation, the system also includes a number of other components including a slicer drive/control 41 for controlling the operation of the slicing blade. This control module may be external to the slicer machine itself or may be embedded in the slicer. The control 41 may be of any suitable design, but in an embodiment of the invention it is an electric drive control of an AC or DC configuration, which controls the speed of the slicer blade, and thus controls the frequency at which new slices are processed. Suitable controls include but are not limited to voltage level controls, current level controls, stepper controls, pulse width modulation controls, and so on, and may, but need not, employ feedback in a speed control loop.

For controlling the first spray nozzle 34a and the optional second spray nozzle 34b, slice nozzle controls 42 are included in the system. If multiple processing chains are run simultaneously, this module may control all of the slice nozzles needed. These controls 42 activate the spray nozzles 34a, 34b based on a trigger signal received from a spray trigger 44. The spray trigger 44 may be of any suitable type, but in an embodiment of the invention the spray trigger 44 is a beam interruption trigger linked to a hole or other space or gap associated with the slicer blade 3, 33 or the drive 41. In a preferred embodiment of the invention, the spray trigger comprises an encoder signal received from the slicer, defining the slicer blade position.

In order to provide the shot of antimicrobial preparation to the vacuum pouch 37 prior to vacuum and sealing, a rollstock pouch nozzle control 46 is provided. As noted above, the timing of this shot is not critical but it is desirable that the shot occur prior to insertion of the stack 38 into the pouch 37.

The antimicrobial preparation is supplied to the various nozzles in pressurized liquid form. A fluid pump 45 pressurizes the fluid from a tank to promote the flow and spray of the fluid. Thus, in order to ensure that the proper amount of preparation is applied, the timing and pressure of the fluid spray must be monitored and the availability of the fluid in the tank must be maintained. To this end, the system includes a tank fluid level sensor, pump fluid pressure sensor, and spray check sensor, represented collectively in FIG. 4 as the fluid level/pressure/spray check sensor 43 module.

The fluid level sensor may be a continuous sensor within the tank (not shown) or a float type sensor. If the fluid level drops below the low float level in the tank for an extended period of time, an audible and/or visible alarm may also be triggered by the system. The fluid pressure sensor may be a P/I transducer or other suitable device for measuring pressure. In an embodiment of the invention, the pressure of the fluid is maintained within a predetermined variance, e.g., 30 PSI. If the pressure exceeds or drops below this tolerance, an alarm may sound, the stack light may activate, and another alarm notification may appear on the touch screen (e.g., on user interface 40 and/or user interface 49). In an embodiment of the invention, the tank is auto-filled on a continuous basis rather than being periodically filled. In a further embodiment of the invention, the tank itself may be pressurized and a pressure relief valve may be used to maintain fluid pressure at a predetermined level during filling operations.

In order to provide the vacuum required to appropriately evacuate the vacuum pouch 37 and uniformly spread the final shot of antimicrobial preparation, a vacuum control 48 manages the application of vacuum pressure to the pouch 37. In an embodiment of the invention, the rollstock machine independently manages this operation and is not tied into the slicer or spray system. In an embodiment of the invention, the vacuum control 48 includes driving circuitry and a solenoid valve. It will be appreciated that other arrangements are possible as well.

To check the pulse duration of the various antimicrobial applications, one or more spray check sensors may be situated near the nozzles 34a, 34b (optional), 34c. The spray check sensors may be optical or otherwise, and provide a signal indicating the duration of the respective shots. If a shot duration varies from its nominal value by more than a predetermined margin for more than a predetermined period of time or number of occurrences, an alarm condition is considered to have occurred, and it is deemed that the necessary amount of preparation was not applied. For example, a sequence of three consecutive non-conforming shots is sufficient to trigger an alarm in an embodiment of the invention.

In a particular embodiment of the invention, deviations above the nominal time may be ignored. In a further related embodiment of the invention, if the registered spray time from the sensor is equal to or greater than 80% of the calculated shot size, this is considered to be a good shot. If the shot size is less than 80% for the required time or number of occurrences, an alarm will be displayed on the stack light and on the touch screen of the unit to identify which nozzle had the alarm.

To provide the necessary alarms to the operator, an alarm module 47 processes information received from the various sensors and provides and audible and/or visual alarm to the operator if an alarm condition is indicated by the sensor values.

In summary, the digital inputs received by the system to operate and to verify correct operation are a spray check sensor signal, a trigger signal (e.g., from a physical push button or thru beam photo eye), a fluid level switch signal (low level tank). In an embodiment of the invention, a level switch is also provided to monitor a low level in a concentrate tank. The digital outputs provided by the system during operation include nozzle on/off signals and alarm signals.

The analog inputs used by the system include a pressure transmitter signal and a continuous level sensor signal where such a sensor is used. The analog outputs provided by the system during operation include primarily the air pressure output control signal where used.

As noted above, it is important to apply the correct amount of antimicrobial preparation to the product to economically and effectively control bacterial outgrowth. In an embodiment, the volume sprayed for each slice ranges from about 0.3 milliliter to about 1 milliliter. In an embodiment of the invention, the operator inputs a shot size in milliliters based on product size and surface area. In an exemplary implementation, each nozzle is a solid stream type nozzle with approximately a 0.123" size orifice. In another embodiment of the invention, the shot sizes vary from 5 milliliters to 40 milliliters. In order to allow high production speed, all shot sizes may be required to be dispensed within a short time period, e.g., 0.5 seconds in an embodiment of the invention.

By way of example, at an operating pressure of 125 PSI, a 0.094" orifice will dispense approximately 0.6 GPM (gallons per minute). The program takes into account the programmed shot size and converts it into a flow rate by using the relationship of $P_1/P_2 = Q_1^{1/2}/Q_2^{1/2}$. Using this formula, a shot time is calculated to deliver the programmed shot size volume.

When an autofilling function and pressurized tank are desired, the program operates by adjusting a programmable pressure set point for the tank. For a whole muscle based system, for example, this pressure is set at 30 PSI. In other applications, the tank is at ambient pressure, and a pump subsequently pressurizes fluid at it exits the tank, e.g., to 120 PSI.

When the tank level falls below a programmed threshold (typically above 5%), more fluid is allowed into the tank. In an embodiment, this action is executed via a mixing pump having an outlet valve connecting into the tank. The mixing pump intakes water and concentrate, and produces the appropriately diluted antimicrobial preparation. The formula for the antimicrobial preparation may vary, e.g., depending upon whether the purpose of the system is to only kill pathogenic bacteria or also to prolong the shelf life of the packaged product.

This auto fill function will allow the tank to start refilling while the system is still in operation. As the pressure starts building in the tank during the refill cycle, the excess air pressure in the tank is bled off by the I/P to ensure that the pressure stays constant during the refill cycle. In a further embodiment of the invention, the system includes a concentrate tank with a low level float type level sensor. If the fluid level drops below the low mark, an audible and visual alarm is activated in the panel.

Figure 5:
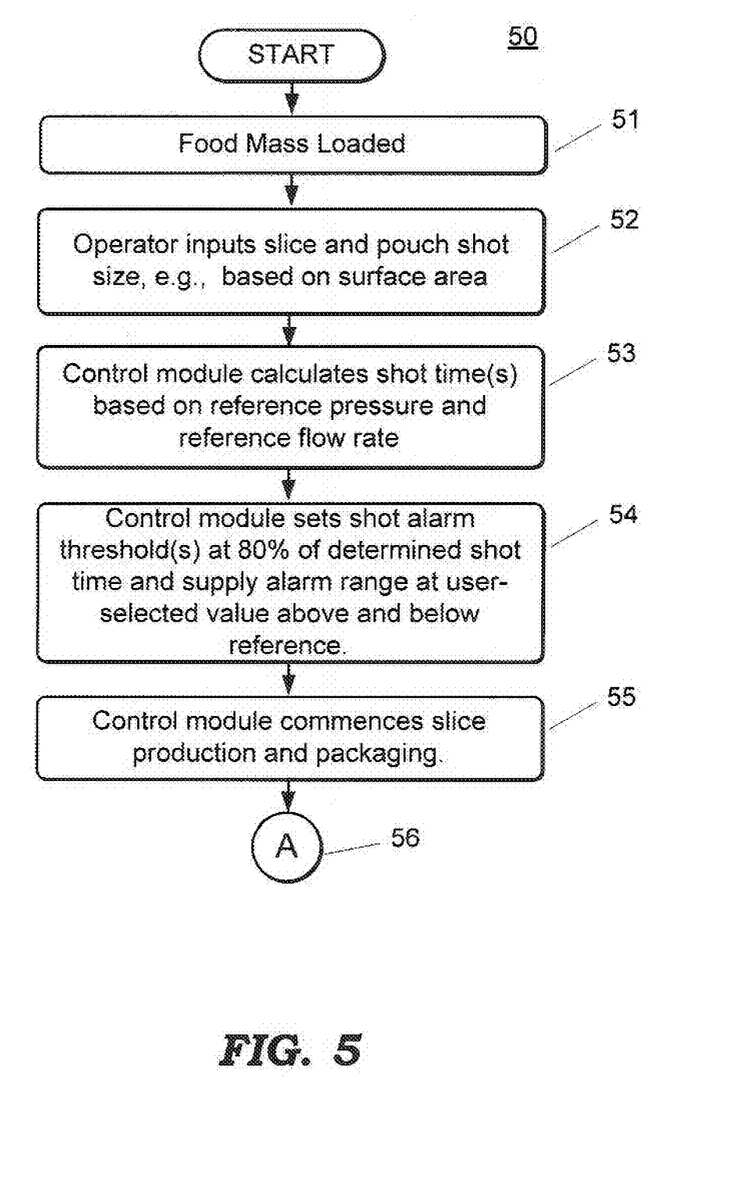
FIG. 5 is a flow chart illustrating a process for initializing a meat processing system in an embodiment of the present invention.
Figure 6:
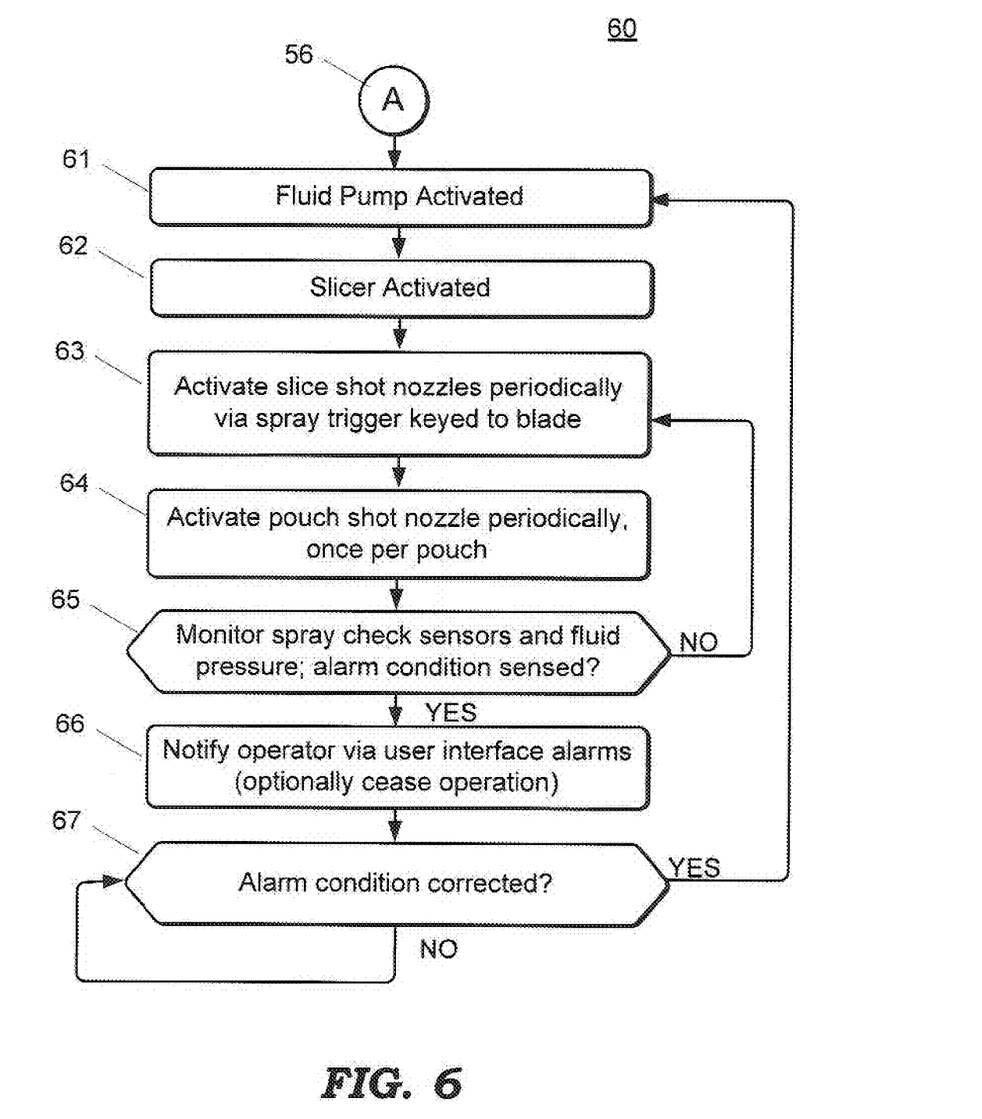
FIG. 6 is a flow chart illustrating a process for meat processing in an embodiment of the present invention.

The process steps discussed herein that are not executed by the operator are executed via computer control, e.g., via a computing device reading computer-executable instructions from a computer-readable medium such as a disk, RAM, ROM, thumb drive, etc. In the description of FIGS. 5 and 6, this will not be repeated at length, but those of skill in the art will be aware that the non-operator executed steps are executed automatically under computer control as described above.

FIG. 5 is a flow chart illustrating a process 50 for initializing a meat processing system in an embodiment of the present invention. At stage 51, a food mass, e.g., a meat log 1, is loaded in the machine. This step will typically be operator-executed, but may also be automated if desired. At stage 52, the operator inputs slice and rollstock/pouch shot size, e.g., based on surface area of the loaded food product. The control module calculates shot times based on reference pressure and reference flow rates at stage 53 in the manner discussed above.

At stage 54, the control module sets shot alarm thresholds at 80% of the determined shot time (or other desired cut-off) and supplies alarm ranges at user-selected values above and below this reference level. At stage 55, the control module commences slice production and packaging. From this stage, the process 50 moves to waypoint A (56).

The process 60, illustrated in the flow chart of FIG. 6, begins from waypoint A (56). At stage 61 of the process 60, the fluid pump activated, and the slicer is activated subsequently at stage 62. The slice shot nozzles are triggered periodically via the spray trigger from the slicing machine at stage 63, and the rollstock/pouch shot nozzle is activated periodically, once per pouch, at stage 64.

As the process progresses, the controller monitors the spray check sensors and fluid pressure and level signals. If an alarm condition is sensed at stage 65, the system may execute a user-selected remedial action. In an embodiment, a manually selectable option allows the process to shut down or to continue operation if alarm condition arises. In either case, the system preferably notifies the operator via user interface alarms at stage 66. Otherwise, the system returns to stage 63 to continue processing.

In the event that an alarm condition was indicated at stage 66, the system awaits correction of the condition at stage 67. If the alarm condition is corrected, the system flows to stage 61 to reinitiate processing. Otherwise, the system loops at stage 67 and continues to await correction of the error condition.

In an alternative embodiment of the invention, the described spray apparatus and system are used, with modifications as reflected below, to treat a mix or blend of material rather than a solid preformed mass of material. For example, it may be desirable to treat batches of beef scraps prior to grinding to reduce the microbial count most efficiently; if the mix is treated after grinding, any bacteria initially on the pieces may become difficult or impossible to reach with the antimicrobial spray. In addition, such materials may be post-treated as well, i.e., after grinding and/or mixing but before being batched out for final packaging.

Figure 7:
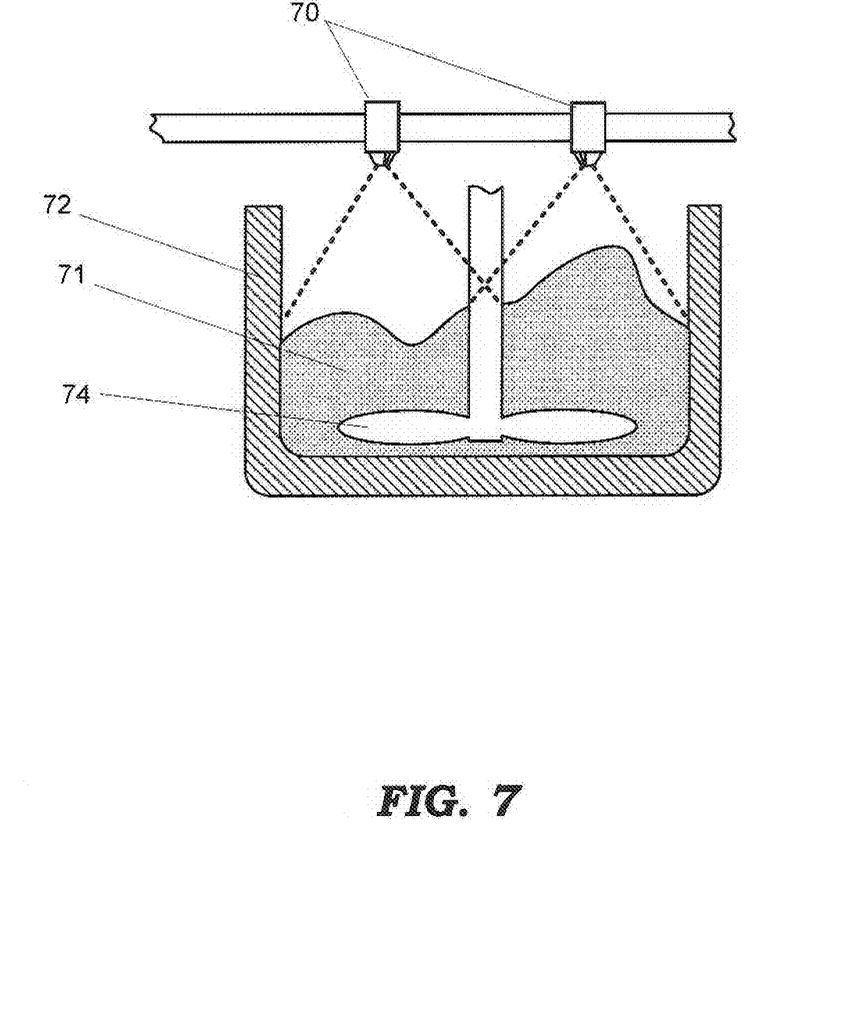
FIG. 7 is a cross-sectional side view of a batch mixing/blending apparatus according to an embodiment of the invention.
Figure 8:
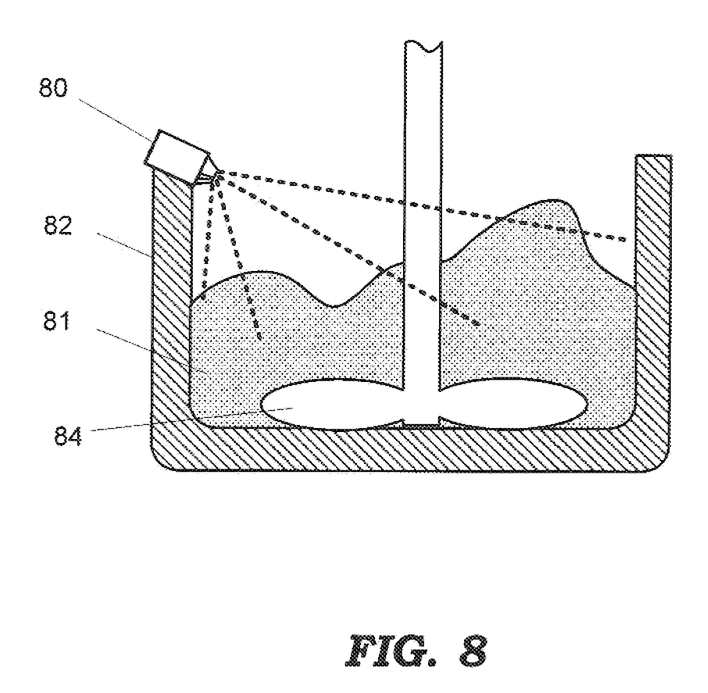
FIG. 8 is a cross-sectional side view of a batch mixing/blending apparatus according to an alternative embodiment of the invention.

In this embodiment, the spray treatment nozzles may be mounted on a ½-inch stainless rod or other mounting hardware to spray into a mixer or blender container. The nozzles include full cone type spray tips in an optional embodiment of the invention. Nozzles 70 may be mounted directly above the product 71 to spray directly down onto the product 71 held by the container 72 as in FIG. 7. Alternatively, as shown in FIG. 8, if the nozzles 80 are mounted to the lip of the container 82, they may be mounted to spray at an angle. In either embodiment, a mixing implement 74, 84 may be provided for mixing or blending the material in the container.

Although any number of different spray tips would be suitable, an exemplary spray tip is the SPRAYING SYSTEMS CO. part number TG1.5W-316SS which is configured to dispense 0.15 GPM at 10 PSI per tip. Regarding the number of spray tips employed, multiple spray tips will generally be used to provide uniform and sufficient coverage of the surface of the product mix 71, 81. In an embodiment of the invention, the nozzles are configured and situated to provide a slight overlap between adjacent nozzle patterns as shown in the patterns 73, 74, 75 of FIG. 7.

The prescribed dosage is typically applied to the product bed on an incremental basis through a timed on/off cycle. The total cycle time will depend on validation testing to ensure proper coverage, but may typically range between 2-8 minutes. The antimicrobial solution is dispensed evenly throughout this entire programmed cycle time in an embodiment of the invention.

Although dosages may differ depending upon the type and concentration of antimicrobial solution used in a given implementation, an average dosage of diluted antimicrobial in an embodiment of the invention is roughly 4 milliliters of solution per pound of meat. Batch sizes of meat may vary widely, e.g., between about 500 lbs and 6000 lbs depending on the size of the mixer blender container 802.

In an embodiment of the invention, each time the nozzles cycle, external sensors (e.g., SPRAYING SYSTEMS SPRAYCHECK sensors) in the manner described above and/or inline flow switches are used to validate that the nozzles did indeed fire during each cycle. In this way, if there is an irregularity in the spray pattern of one or more nozzles or if one or more nozzles become plugged, the sensor will provide feedback to the control panel, which will output a visual and audible alarm.

In order to ensure proper dosage of fluid for each batch of meat, a flow meter is also utilized in an embodiment of the invention to provide precise flow deposition for each batch. In an embodiment, the system operator is able to program the correct flow requirement per batch in the HMI based on antimicrobial dosage and batch size.

Figure 9:
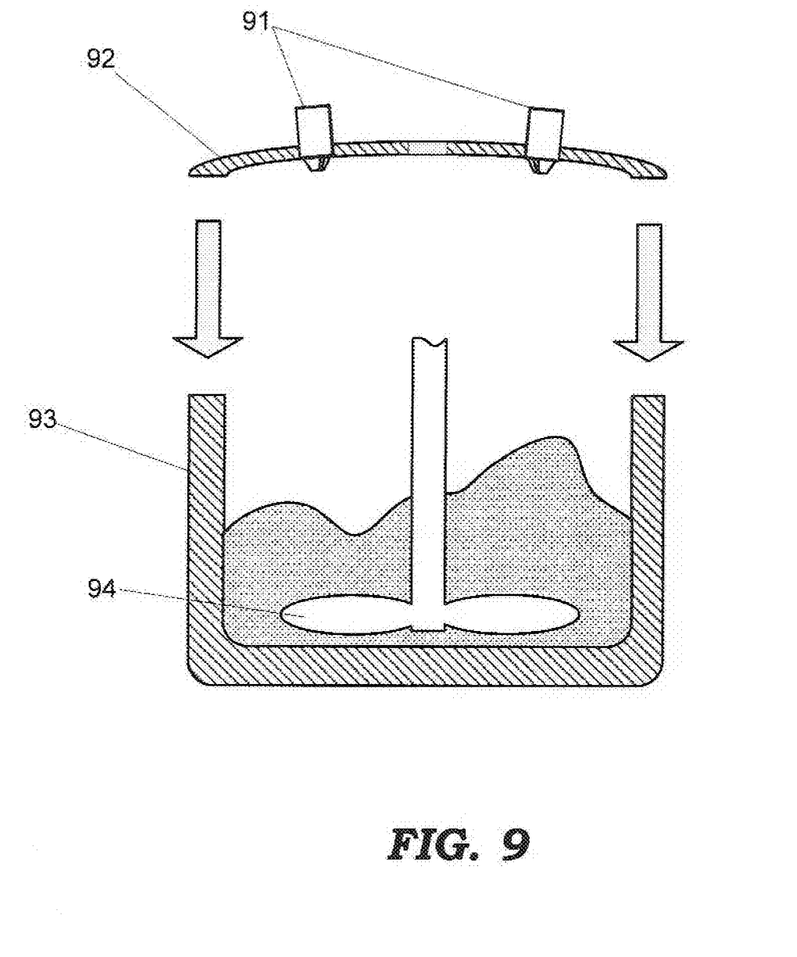
FIG. 9 is a cross-sectional side view of a batch mixing/blending apparatus according to an embodiment of the invention wherein a lid is provided for containing a cold treatment substance such as liquid $CO_2$ or otherwise.

In order to cool the meat or other material of interest after mixing, the mixer blender is also configured to inject either liquid $CO_2$ or $N_2$ into the mixer in an embodiment of the invention. In this embodiment, the nozzles 91 may be mounted through the lid 92 of the mixer container 93 as shown in FIG. 9 to allow just the nozzle tips to stick through. Again the nozzles 91 may be spaced evenly to provide complete coverage over the product bed. A mixing implement 94 such as a bladed implement is provided for mixing or blending the material within the container.

In a further embodiment of the invention, the antimicrobial solution is applied to the batch after any appropriate spices and/or flavors are added and mixed. Following this spice/flavor application, the antimicrobial solution is dispensed based on a pretested timed cycle to ensure coverage. Once the antimicrobial solution has been dispensed, a compressed air or nitrogen purge of the nozzles is conducted prior to commencement of the CO2 or N2 cycle. This ensures that all moisture exits the nozzle tips prior to the gas injection to prevent freezing and clogging of the tips. Once the CO2 or Nitrogen cycle is completed, the product is taken to a forming machine to shape the meat for packaging.

In certain cases, the antimicrobial solution may be sensitive to temperature drops, e.g., resulting in the chemical precipitating out of solution. Thus in an embodiment of the invention, an insertion type heater may be placed in the pressure vessel with an agitator to ensure thorough heat transfer. The temperature control for the heater will be utilizing a PID algorithm in order to maintain a specific setpoint temperature as set on the control screen HMI.

In certain implementations, the compressed air or nitrogen purge may be impractical to implement or ineffective in resolving nozzle freezing problems resulting from the CO2 or liquid Nitrogen injection. Thus, in a further embodiment of the invention, jacketed nozzles (e.g., SPRAYING SYSTEMS PULSEJETS) can be alternatively or additionally utilized to ensure the nozzle tips do not freeze during cycles. In a further embodiment, the jacketed nozzles employ a water recirculation jacket surrounding each nozzle to keep the temperature at the tip at a user programmed set point. The liquid delivery unit for the jacketing fluid includes an insertion type heater, centrifugal pump, and stand pipe fluid reservoir in an embodiment of the invention.

It will be appreciated that the structures and process presented herein enable and new and more efficient way to process sliced food products. All references herein, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A system for preparing packages of sliced food product from a piece of said food product while minimizing bacterial contamination and outgrowth within the packaged food product, the system comprising:

a powered slicer having a blade;

a support for holding the piece of food product and moving it gradually into the blade of the powered slicer, the blade acting to sequentially separate slices of the food product from the piece of food product to create a stack of food product slices, each having a forward face and a reverse face with an exposed face of the piece of food product from which the slices are cut becoming the forward face of the next slice, said slicer being operable to operate the blade at a rate of up to 1,500 revolutions per minute such that the powered slicer produces up to 1,500 slices per minute;

a fluid source for providing a liquid antimicrobial preparation;

a first variable speed pulsating spray nozzle for depositing a first predetermined amount of the antimicrobial preparation only onto the forward face of each slice each time a slice is removed from the piece of food product such that the reverse face remains untreated with said antimicrobial preparation as it falls into the stack and the antimicrobial preparation sprayed onto the forward face is spread by contact onto the untreated reverse face of the preceding slice sufficient for effectively treating the reverse face of the slice against bacterial contamination;

said pulsating nozzle being intermittently operated based upon the operating speed of the slicer blade for providing a predetermined pulse and quantity of antimicrobial preparation onto the forward face of each slice for the particular operating rate of the slicer blade;

a control for controlling the frequency and duration of the pulse of the first spray nozzle for a particular slicing operation of the food product;

a vacuum pouch system for providing a vacuum pouch to receive each stack of food product slice; and a second spray nozzle for depositing a second predetermined amount of the antimicrobial preparation into each vacuum pouch prior to reception of a stack within the pouch;

wherein the second predetermined amount of the antimicrobial preparation deposited into each vacuum pouch is configured to coat a second face of the topmost slice in each stack and the side faces of all slices in each stack, which were previously untreated.

2. The system for preparing packages of sliced food product according to claim 1, further comprising a vacuum pump for applying a vacuum to each vacuum pouch after reception of a stack within the pouch such that the second predetermined amount of the antimicrobial preparation is substantially evenly spread over an external surface of the stack.

3. The system for preparing packages of sliced food product according to claim 1, wherein the first spray nozzle is intermittently activated based on a position of the blade of the powered slicer.

4. The system for preparing packages of sliced food product according to claim 1, wherein the fluid source for providing a liquid antimicrobial preparation further comprises a first tank providing liquid antimicrobial preparation to the first spray nozzle and a second tank providing liquid antimicrobial preparation to the second spray nozzle.

5. The system for preparing packages of sliced food product according to claim 4, wherein the first tank is at a first pressure and the second tank is at a second pressure different from the first pressure.

6. The system for preparing packages of sliced food product according to claim 5, further comprising a liquid pump between the first tank and the first spray nozzle for providing a pressurized flow of liquid antimicrobial preparation to the first spray nozzle.

7. The system for preparing packages of sliced food product according to claim 1, further comprising a spray check sensor associated with the first spray nozzle to determine the duration of spray shots emanating from the first spray nozzle.

8. The system for preparing packages of sliced food product according to claim 7, further comprising an alarm module for notifying an operator of the system if the spray check sensor associated with the first spray nozzle detects a predetermined alarm condition.

9. The system for preparing packages of sliced food product according to claim 8, wherein the predetermined alarm condition identifies a number of consecutive spray occurrences delivering less than a predetermined amount of the antimicrobial preparation.

10. The system according to claim 1 including a computer-readable medium having thereon computer-executable instructions to trigger the first spray nozzle to deposit said first predetermined amount of the antimicrobial preparation only onto the forward face each time a slice is removed from the piece of food product.

11. The system according to claim 10, further comprising a vacuum pump and wherein the computer-readable medium further includes computer-executable instructions to apply a vacuum to each vacuum pouch after reception of a stack within the pouch such that the second predetermined amount of the antimicrobial preparation is substantially evenly spread over an external surface of the stack.

12. The system according to claim 10, wherein the computer-executable instructions to trigger the first spray nozzle comprise instructions to trigger the first spray nozzle intermittently based on a position of the blade of the powered slicer.

13. The system according to claim 12, wherein the computer-executable instructions to trigger the second spray nozzle comprise instructions to trigger the second spray nozzle intermittently.

14. The system according to claim 10, wherein the fluid source for providing a liquid antimicrobial preparation further comprises a first tank providing liquid antimicrobial preparation to the first spray nozzle and a second tank providing liquid antimicrobial preparation to the second spray nozzle, said first tank being at a first pressure and the second tank being at a second pressure different from the first pressure, a liquid pump between the first tank and the first spray nozzle, said computer-readable medium further comprising computer-executable instructions for activating the liquid pump to provide a pressurized flow of liquid antimicrobial preparation to the first spray nozzle.

15. The system according to claim 10, further comprising a spray check sensor associated with the first spray nozzle to determine the duration of spray shots emanating from the first spray nozzle, said computer-readable medium further comprises computer-executable instructions for notifying an operator of the system if the spray check sensor associated with the first spray nozzle detects a predetermined alarm condition that identifies a number of consecutive spray occurrences delivering less than a predetermined amount of the antimicrobial preparation.

16. The system for preparing packages of sliced food product according to claim 1 in which said control calculates the predetermined quantity of antimicrobial preparation during each pulse based upon the pressure of the liquid antimicrobial preparation to said first spray nozzle.

17. The system according to claim 1 in which said first variable speed pulsating spray nozzle is operated by said control for directing said antimicrobial preparation onto less than 100% of the forward face of each slice.

18. The system according to claim 17 in which said variable speed pulsating spray nozzle is operated by said control for directing said antimicrobial preparation onto about 80% of the surface area of the first face of each slice.

19. The system according to claim 1 in which said powered slicer blade is operated with rotational or oscillating movement, and said first variable speed pulsating nozzle is intermittently operated to direct said antimicrobial preparation onto the first face of each slice only when the slicer blade is between each revolution or oscillation.

20. The system according to claim 19 including a sensor for providing a signal indicating the position of the slicer blade during rotational or oscillating movement.

\* \* \* \* \*